United States Patent [19]

Mookherjee et al.

[11] 4,282,274
[45] Aug. 4, 1981

[54] ORGANOLEPTIC USES OF 2- AND 3-CYCLOTETRADECEN-1-ONES

[75] Inventors: Braja D. Mookherjee, Holmdel; Robert W. Trenkle, Bricktown; Manfred H. Vock, Locust; Domenick Luccarelli, Jr., Ocean; Frederick L. Schmitt, Holmdel; Gilbert Stork, Englewood, all of N.J.; Timothy MacDonald, Nashville, Tenn.; Arthur L. Lieberman, Highlands, N.J.

[73] Assignee: International Flavors & Fragrances Inc., New York, N.Y.

[21] Appl. No.: 52,668

[22] Filed: Jun. 27, 1979

Related U.S. Application Data

[62] Division of Ser. No. 973,093, Dec. 26, 1978, Pat. No. 4,183,965.

[51] Int. Cl.$^3$ .................. C11D 17/04; C11D 17/06
[52] U.S. Cl. .................................. 427/402; 15/208; 252/8.6; 252/90; 252/91; 424/19; 424/25; 424/27; 427/416; 428/262; 428/264; 428/289; 428/484; 428/486; 428/537; 428/905
[58] Field of Search ................................. 15/105, 208; 252/8.6–8.9, 90, 91; 427/242, 402, 416; 428/136, 304–307, 905, 260, 262, 264, 284, 289, 484, 486, 537; 424/14, 16, 19, 25, 27, 31, 38

[56] References Cited

U.S. PATENT DOCUMENTS

| | | | |
|---|---|---|---|
| 1,702,852 | 2/1929 | Ruzicka | 260/586 M |
| 1,873,154 | 8/1932 | Ruzicka | 260/586 M |
| 2,656,391 | 10/1953 | Stoll | 260/586 M |
| 3,235,601 | 2/1966 | Parsons et al. | 260/586 M |
| 3,632,396 | 1/1972 | Parez-Zamora | 428/303 |

FOREIGN PATENT DOCUMENTS

235540  4/1926  United Kingdom ............... 260/586 M

OTHER PUBLICATIONS

Arctander, Perfume and Flavor Chemicals, vol. I, 1969, Montclair, N. J. item No. 813.

Stork et al., Journal of American Chemical Society, vol. 97, No. 5, Mar. 5, 1975, pp. 1264 and 1265.

*Primary Examiner*—Bruce H. Hess
*Attorney, Agent, or Firm*—Arthur L. Liberman

[57] ABSTRACT

Processes and compositions are described for the use in foodstuff flavor and aroma and perfume and perfumed article aroma augmenting, modifying, altering and enhancing compositions and as foodstuff, chewing gum, toothpaste, medicinal product, perfume and perfumed article aroma imparting materials of specific isomer and isomer mixtures of 2- and 3-cyclotetradecen-1-ones having the structures:

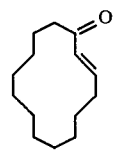

and 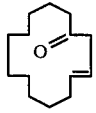

(trans isomer)  (mixture of cis and trans isomers)

or mixtures of same or mixtures of such 2- and 3-cyclotetradecen-1-ones with cyclotetradecanone having the structure:

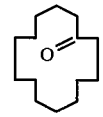

or cyclododecanone having the structure:

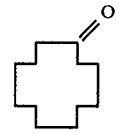

Addition of said 2- and 3-cyclotetradecen-1-ones or mixtures is indicated to produce:

(a) In food flavorings, a sweet, brown sugar and musky aroma and sweet and musky flavor characteristics (useful for flavor augmentation or enhancement in pear, blackberry, apricot and peach flavors and as a bitterness depressant for such foodstuffs, flavor adjuvants and beverages as black coffee; and (b) In perfumes and perfumed articles, a sweet, musk aroma and exaltone-like, scorched linen, waxy and rooty nuances.

1 Claim, 5 Drawing Figures

IR SPECTRUM FOR EXAMPLE I, PEAK 2

IR SPECTRUM FOR EXAMPLE I, PEAK 3.

ORGANOLEPTIC USES OF 2- AND 3-CYCLOTETRADECEN-1-ONES

This application is a divisional of application for U.S. Letters Patent, Ser. No. 973,093, filed on Dec. 26, 1978, now U.S. Pat. No. 4,183,965 issued Jan. 15, 1980.

BACKGROUND OF THE INVENTION

The present invention relates to 2- and 3-cyclotetradecen-1-ones and mixtures containing same as well as organoleptic uses thereof to alter, modify, augment, enhance or impart flavors and/or aromas in (or to) consumable materials.

There has been considerable work performed relating to substances which can be used to impart (or alter, modify, or enhance) flavors and fragrances to (or in) various consumable materials. These substances are used to diminish the use of natural materials, some of which may be in short supply and to provide more uniform properties in the finished product. Sweet, brown sugar-like and musky aroma characteristics and sweet, musky flavor characteristics are particularly desirable for many uses in foodstuff flavors, particularly, pear, blackberry, apricot and peach flavors. Musky aromas are desirable in several types of perfume compositions and for use in perfumed articles.

The 2- and 3-cyclotetradecen-1-ones of our invention prepared according to the process disclosed by Stork and Macdonald at pages 1264 and 1265 of the Journal of the American Chemical Society, Vol. 97, No. 5, Mar. 5, 1975 are musk odorants and as such are highly desirable in the perfumery and aroma chemical area. The odor of musk is perhaps the most universally appreciated fragrance and is usually thought of as the animal note in perfumes. A number of naturally occurring species, both of animal and vegetable origin possess musk odors; however, only three animal sources have achieved any commercial importance. It is because of the high demand and short supply of these naturally occurring musk odorants that numerous attempts have been made since the 1920's to synthesize compounds which would duplicate these desirable odors.

Cyclotetradec-2-ene-1-one (without specifying the geometric isomeric configuration thereof) is disclosed to be produced by Leonard and Owens, J. Am. Chem. Soc. 80, 6039-45 (1958).

7-Cyclotetradecene-1-one, a homologue of civetone which is a constituent of an oil secreted by the civet cat is known to be a valuable perfume base. The determination of the gross structure of civetone was accomplished by Ruzicka and co-workers (Helv. Chim. Acta., 9,230 [1926] and 10, 695 [1029]). In 1948, Stoll and co-workers (Helv. Chim. Acta., 31, 543 [1948] proved that naturally occurring civetone has a "cis" configuration.

Trans-7-cyclotetradecene-1-one, the aforementioned civetone homologue was prepared by Parsons and Pittman as disclosed in U.S. Pat. No. 3,235,601 issued on Feb. 15, 1966. Stoll in U.S. Pat. No. 2,656,391 disclosed a process for the preparation of alpha,beta unsaturated cyclopolymethylenic ketones, both alkylated and not alkylated having from 10 to 18 carbon atoms in the ring. Specifically disclosed are alpha,beta cyclohexadecenone (Example I), 15-methylcyclopentadecanol-2-one-1 and cyclodecanolone-1,2 (Example III).

Nothing in the prior art, however, discloses the perfumery or flavor uses of the 2- and 3-cyclotetradecen-1-ones having the structures:

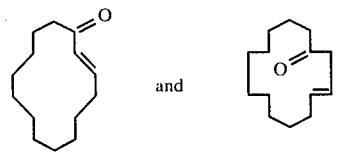

or mixtures of 2- and 3-cyclotetradecen-1-ones as such, or further taken together with either the compound cyclotetradecanone having the structure:

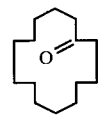

or cyclododecanone having the structure:

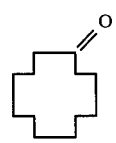

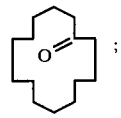

peak 2 represents the compound having the structure:

and peak 3 represents the compound having the structure:

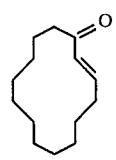

Figure 2:
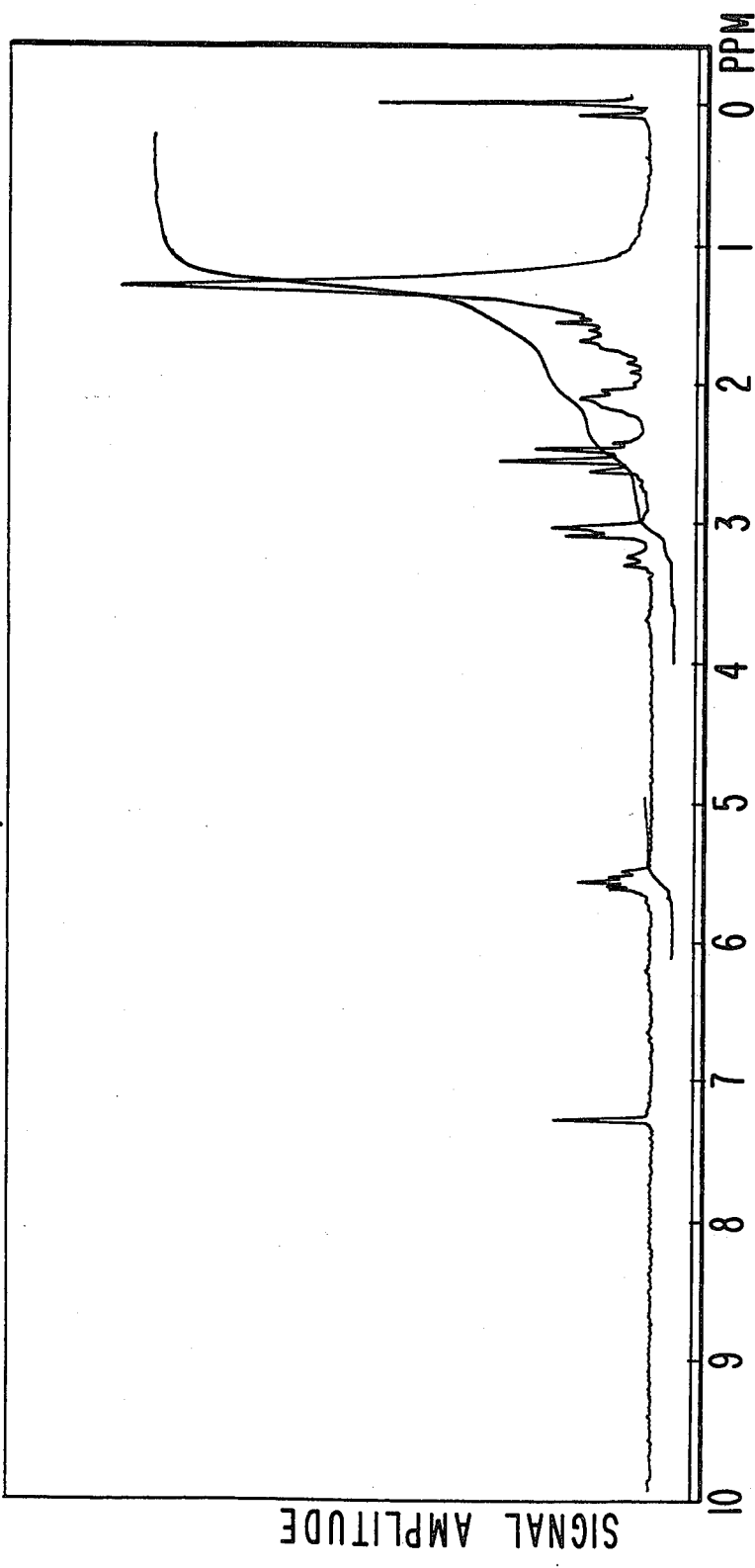

FIG. 2 is the NMR spectrum for peak 2 of the GLC profile of the reaction product produced according to Example I, for the compound having the structure:

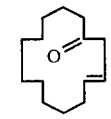

Figure 3:
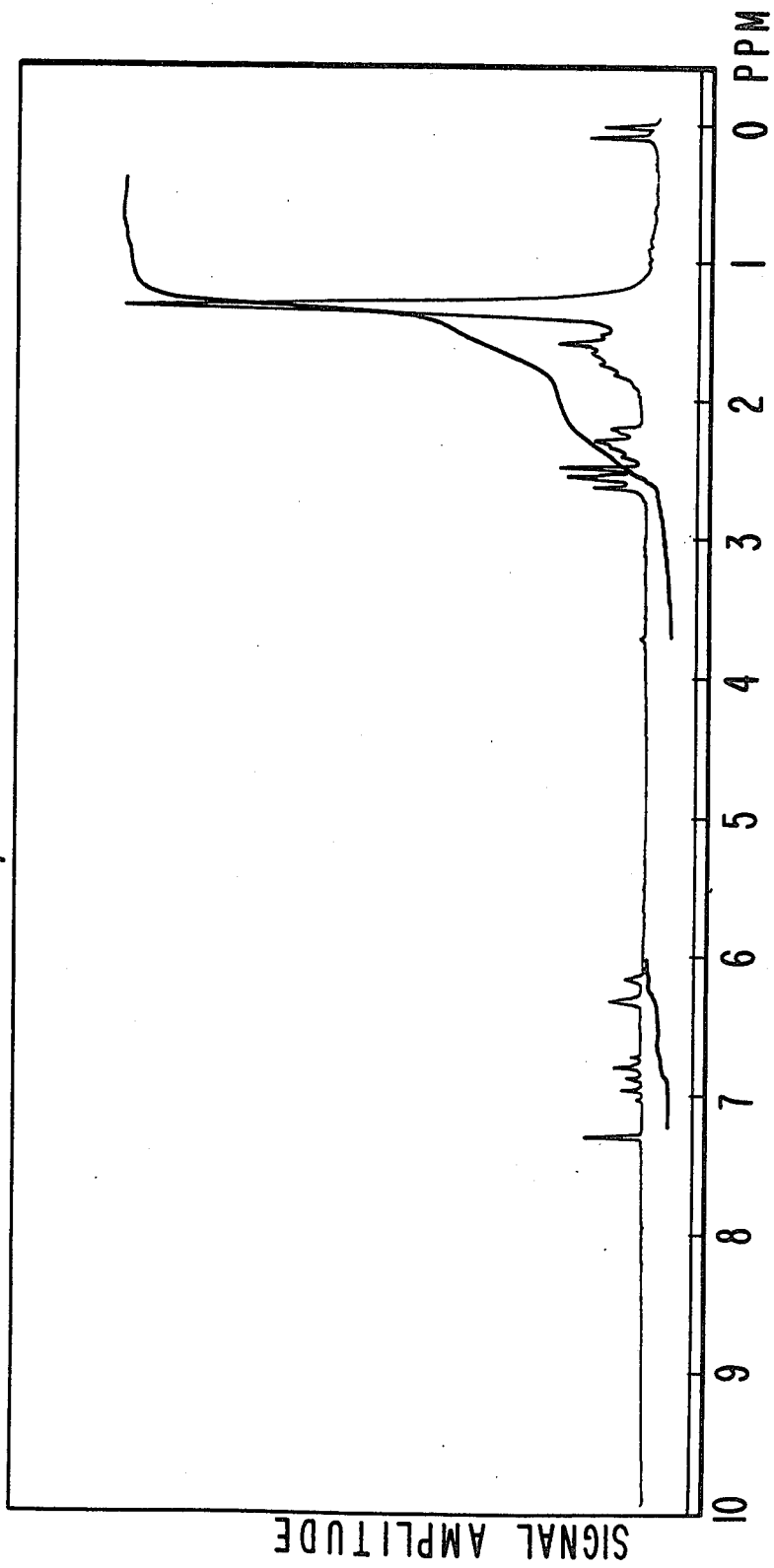

FIG. 3 is the NMR spectrum for peak 3 of the GLC profile of the reaction product produced according to Example I and represents the compound having the structure:

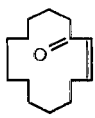

Figure 4:
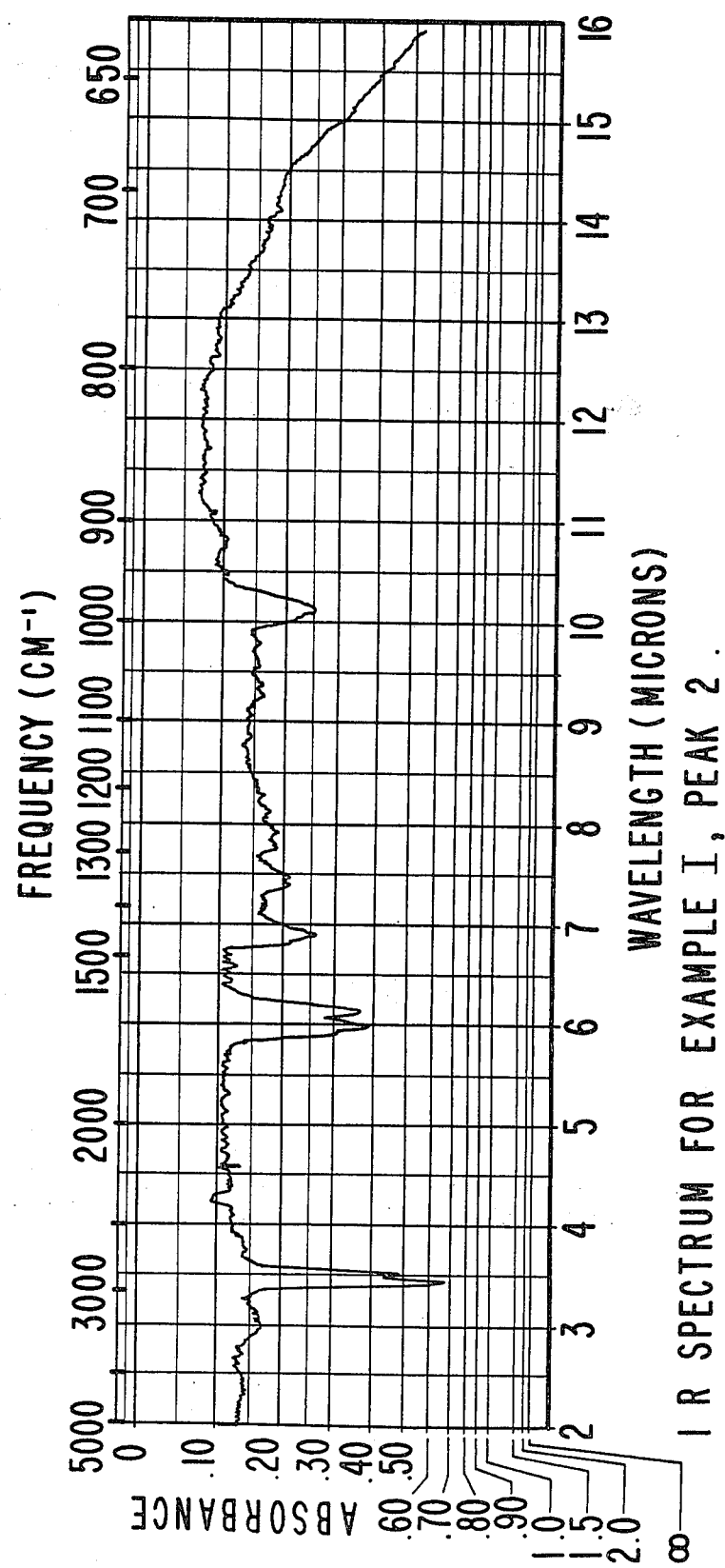

FIG. 4 is the infrared spectrum for peak 2 of the GLC profile of the reaction product produced according to Example I.

Figure 5:
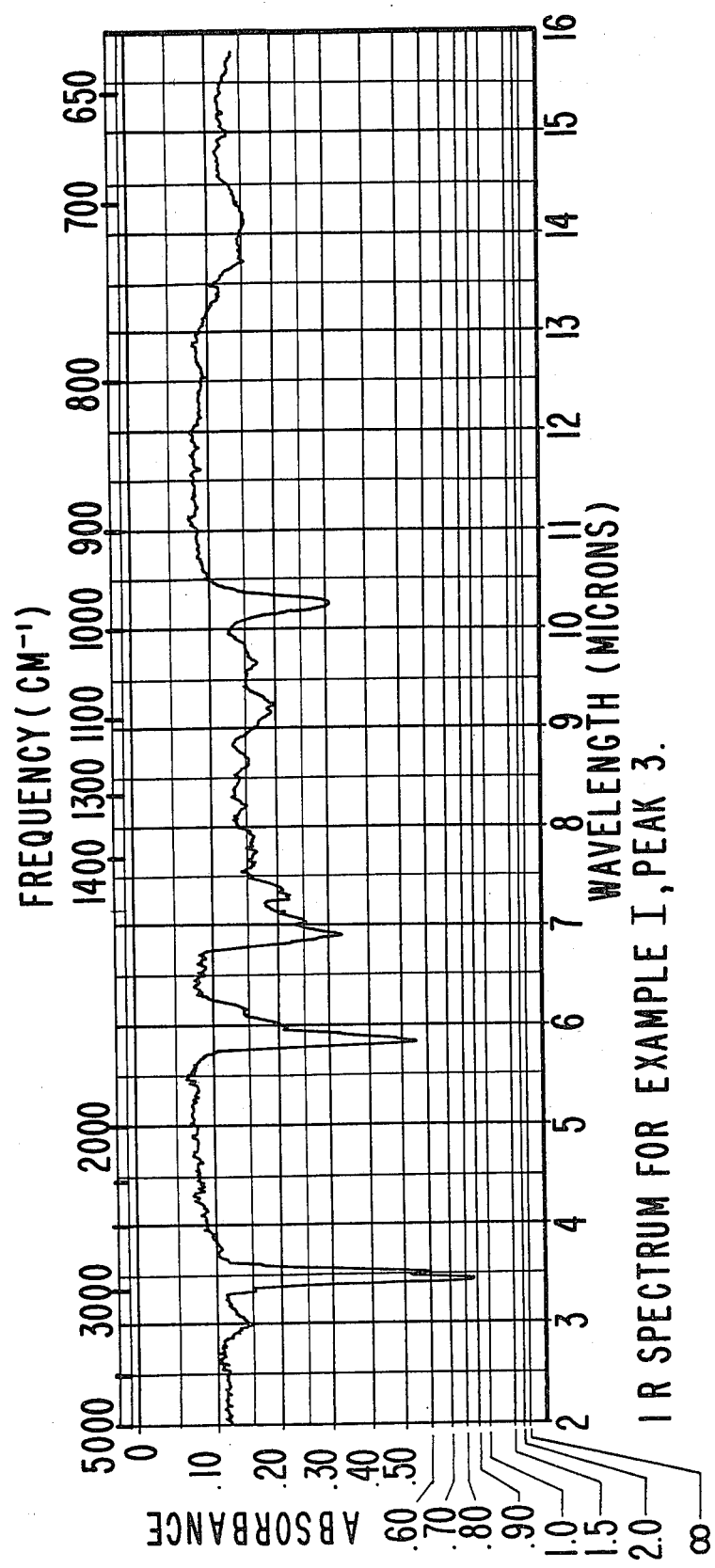

FIG. 5 is the infrared spectrum for peak 3 of the GLC profile of the reaction product produced according to Example I.

THE INVENTION

It has now been discovered that novel solid and liquid foodstuff, chewing gum, medicinal products and flavoring compositions having pear, blackberry, peach or apricot flavors with sweet, brown sugar and musky aroma characteristics and sweet and musky flavor characteristics and novel perfume compositions and perfumed articles having sweet, musky aromas with exaltone-like, scorched linen, waxy and rooty nuances may be provided by 2- and 3-cyclotetradecen-1-ones having the structures:

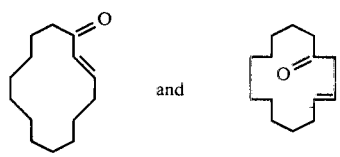

or mixtures of same or mixtures of such 2- and 3-cyclotetradecen-1-ones with cyclotetradecanone having the structure:

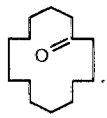

or cyclododecanone having the structure:

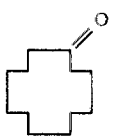

The 2- and 3-cyclotetradecen-1-ones of our invention having the structures:

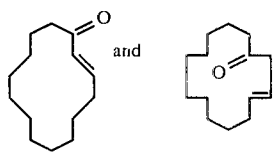

may be prepared according to the process as indicated on pages 1264 and 1265 of the Journal of the American Chemical Society, Vol. 97, No. 5, Mar. 5, 1975 (Stork and Macdonald) as illustrated in the following reaction sequence:

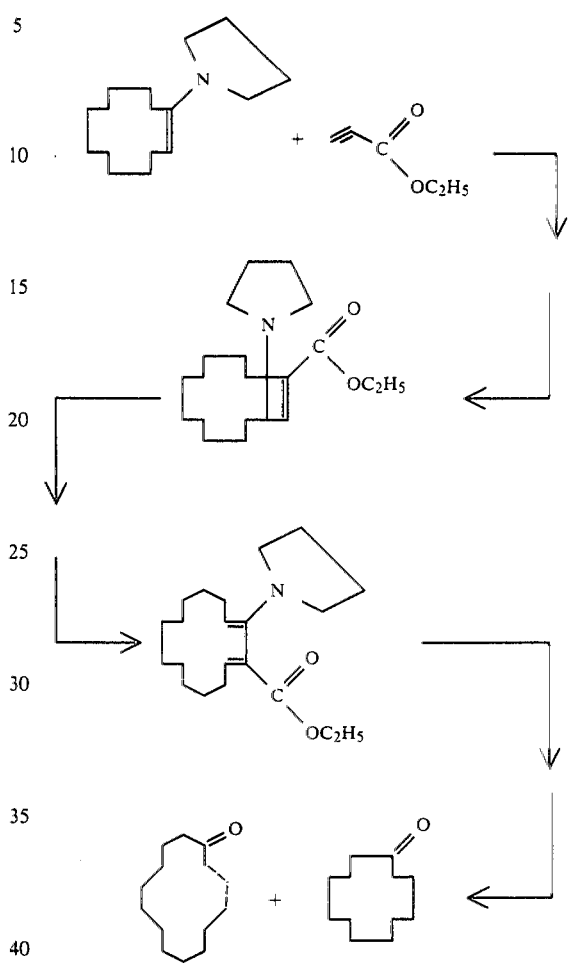

wherein one of the dashed lines represents a carbon-carbon double bond and the other of the dashed lines represents a carbon-carbon single bond and wherein there is produced a mixture of the compounds having the structures:

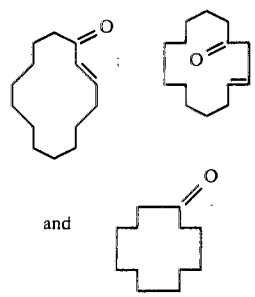

The 2- and 3-cyclotetradecen-1-ones of our invention are capable of supplying and/or potentiating certain flavor and aroma notes usually lacking in many fruit flavors, particularly peach flavors, apricot flavors, blackberry flavors and pear flavors. Furthermore, the 2- and 3-cyclotetradecen-1-ones of our invention are capable of suppressing the bitterness of coffee when added to black coffee at very low levels, e.g., 0.001 ppm or when added in solution to coffee grounds prior to solvent extraction thereof, or they are capable of suppressing the bitterness of foodstuffs and other flavor adjuvants, such as, saccharin or hops. In addition, the 2- and 3-cyclotetradecen-1-ones of our invention are capable of supplying certain fragrance notes usually lacking in many perfume materials, for example, musk fragrances. The double bond isomers of the 2- and 3-cyclotetradecen-1-ones of our invention have the following perfume properties:

| COMPOUND STRUCTURE | ORGANOLEPTIC PROPERTY |
| --- | --- |
| (structure) | A musky, scorched linen, waxy and rooty aroma profile |
| (structure) | A strong sweet musk, exaltone-like aroma profile |

When the 2- and 3-cyclotetradecen-1-ones of our invention are used as food flavor adjuvants, the nature of the co-ingredients included with said 2- and 3-cyclotetradecen-1-ones in formulating the product composition will serve to alter the organoleptic characteristics of the ultimate foodstuff treated therewith.

As used herein in regard to flavors, the terms "alter" and "modify" in their various forms means "supplying or imparting flavor character or note to otherwise bland, relatively tasteless substances or augmenting the existing flavor characteristic where a natural flavor or synthetic flavor or mixture of natural and synthetic flavors is deficient in some regard, or supplementing the existing flavor impression to modify its quality, character or taste".

As used herein, the term "enhance" is intended to mean the intensification (without effecting a change in kind of quality or aroma or taste) of one or more taste and/or aroma nuances present in the organoleptic impression of a consumable material, e.g., foodstuff, tobacco, chewing gum, medicinal product, perfume composition or perfumed article.

As used herein, the term "foodstuff" includes both solid and liquid ingestible materials which usually do, but need not, have nutritional value. Thus, foodstuffs include soups, convenience foods, beverages, dairy products, candies, vegetables, cereals, soft drinks, snacks and the like.

As used herein, the term "chewing gum" is intended to mean a composition which comprises a substantially water-insoluble, chewable plastic gum base such as chicle, or substitutes therefor, including jelutung, guttakay rubber and/or certain comestible natural or synthetic resins or waxes. Incorporated within the gum base, in admixture therewith may be plasticizers or softening agents, e.g., glycerine; and a flavoring composition which incorporates the 2- and 3-cyclotetradecen-1-ones of our invention, and, in addition, sweetening agents which may be sugars, including sucrose or dextrose and/or artificial sweeteners including dipeptides, cyclamates and saccharin. Other optional ingredients may also be present.

The term "medicinal product" includes both solids and liquids which are ingestible, non-toxic materials having medicinal value such as cough syrups, cough drops, toothpaste, aspirin and chewable medicinal tablets as further exemplified herein.

Substances suitable for use herein as co-ingredients or flavoring adjuvants are well known in the art for such use being extensively described in the relevant literature. Such material is required to be "ingestibly" acceptable and thus non-toxic or otherwise non-deleterious. Particularly critical is the additional requirement that such material be organoleptically compatible with the 2- and 3-cyclotetradecen-1-ones encompassed within the scope of our invention. Also critical is the additional requirement that such material be nonreactive (within the range of storage conditions and room temperature use conditions) with 2- and 3-cyclotetradecen-1-ones.

Accordingly, such materials which may in general be characterized as flavoring adjuvants or vehicles comprise broadly stabilizers, thickeners, surface active agents, conditioners, other flavorants and flavor intensifiers.

Stabilizer compounds include preservatives, e.g., sodium chloride; antioxidants, e.g., calcium and sodium ascorbate, ascorbic acid, butylated hydroxyanisole (mixture of 2- and 3-tertiary-butyl-4-hydroxyanisole), butylated hydroxy toluene, (2,6-di-tertiary-butyl-4-methyl phenol), propyl gallate and the like and sequestrants, e.g., citric acid.

Thickener compounds include carriers, binders, protective colloids, suspending agents, emulsifiers, and the like, e.g., agaragar, carrageenan; cellulose and cellulose derivatives such as carboxymethyl cellulose and methyl cellulose; natural and synthetic gums such as gum arabic, gum tragacanth; gelatin, proteinaceous materials; lipids, carbohydrates, starches, pectins, and emulsifiers, e.g., mono- and diglycerides of fatty acids, skim silk powder, hexoses, pentoses, disaccharides, e.g., sucrose, corn syrup and the like.

Surface active agents include emulsifying agents, e.g., fatty acids such as capric acid, caprylic acid, palmitic acid, myristic acid and the like, mono- and diglycerides of fatty acids, lecithin, defoaming and flavor-dispersing agents, such as sorbitan monostearate, potassium stearate, hydrogenated tallow alcohol and the like.

Conditioners include compounds such as bleaching and maturing agents, e.g., benzoyl peroxide, calcium peroxide, hydrogen peroxide and the like; starch modifiers such as peracetic acid, sodium chlorite, sodium hypochlorite, propylene oxide, succinic anhydride and the like, buffers and neutralizing agents, e.g., sodium acetate, ammonium bicarbonate, ammonium phosphate, citric acid, lactic acid, vinegar and the like; colorants, e.g., carminic acid, cochineal, turmeric and curcuma and the like, firming agents such as aluminum sodium sulfate, calcium chloride and calcium gluconate; texturizers, anti-caking agents, e.g., aliminum calcium sulfate and tribasic calcium phosphate; enzymes, yeast foods, e.g., calcium lactate and calcium sulfate; nutrient supplements, e.g., iron salts such as ferric phosphate, ferrous gluconate and the like, riboflavin, vitamins, zinc sources such as zinc chloride, zinc sulfate and the like.

Other flavorants and flavor intensifiers include organic acids, e.g., acetic acid, formic acid, 2-hexenoic acid, benzoic acid, n-butyric acid, caproic acid, caprylic acid, cinnamic acid, isobutyric acid, isovaleric acid, alpha-methyl-butyric acid, propionic acid, valeric acid, cis and trans 2-methyl-2-pentenoic acid, and cis and trans 2-methyl-3-pentenoic acid; ketones and aldehydes, e.g., acetaldehyde, acetophenone, acetone, acetyl methyl carbinol, acrolein, n-butanal, crotonal, diacetyl, beta, beta-dimethyl-acrolein, n-hexanal, 2-hexenal, cis-3-hexenal, 2-heptenal, 4-(p-hydroxyphenyl)-2-butanone, alpha-ionone, beta-ionone, methyl-3-butanone, 2-pentanone, 2-pentenal and propanal; alcohols such as 1-butanol, benzyl alcohol, 1-borneol, trans-3-buten-1-ol, ethanol, geraniol, 1-hexanol, 2-heptenol-1, trans-3-hexenol-1, cis-3-hexen-1-ol, 3-methyl-3-buten-1-ol, 1-penten-2-ol, 1-penten-3-ol, p-hydroxyphenyl-2-ethanol, isoamyl alcohol, isofenchyl alcohol, phenyl-2-ethanol, alpha-terpineol, cis-terpineol hydrate; esters, such as butyl acetate, ethyl acetate, ethyl acetoacetate, ethyl benzoate, ethyl butyrate, ethyl caproate, ethyl cinnamate, ethyl crotonate, ethyl formate, ethyl isobutyrate, ethyl isovalerate, ethyl alpha-methylbutyrate, ethyl propionate, ethyl salicylate, trans-2-hexenyl acetate, hexyl acetate, 2-hexenyl butyrate, n-hexyl butyrate, isoamyl acetate, isopropyl butyrate, methyl acetate, methyl-n-butyrate, methyl caproate, methyl isobutyrate, alpha-methyl-n-butyrate, n-propyl acetate, n-amyl acetate, n-amyl-n-butyrate, benzyl salicylate, dimethyl anthranilate, ethyl methylphenylglycidate, ethyl succinate, isobutyl cinnamate, and terpenyl acetate; lactones, such as delta-decalactone, delta-undecalactone, delta-nonyl-lactone, gamma-undecalactone, gamma-dodecalactone and gamma nonyl-lactone as well as "peach" lactones; essential oils, such as jasmine absolute, rose absolute, orris absolute, lemon essential oil, Bulgarian rose, yara yara, natural raspberry oil and vanilla; sulfides, e.g., methyl sulfide and other materials such as maltol, acetoin and acetals (e.g., 1,1-diethoxyethane, 1,1-dimethoxyethane and dimethoxymethane).

The specific flavoring adjuvant selected for use may be either solid or liquid depending upon the desired physical form of the ultimate product, i.e., foodstuff whether simulated or natural, and should, in any event, be capable of providing an environment in which the 2- and 3-cyclotetradecen-1-ones can be dispersed or admixed to provide a homogeneous medium. In addition, selection of one or more flavoring adjuvants, as well as the quantities thereof will depend upon the precise organoleptic character desired in the finished product. Thus, in the case of flavoring compositions, ingredient selection will vary in accordance with the foodstuff to which the flavor and aroma are to be imparted. In contradistinction, in the preparation of solid products, e.g., simulated foodstuffs, ingredients capable of providing normally solid compositions should be selected such as various cellulose derivatives.

As will be appreciated by those skilled in the art, the amount of 2- and 3-cyclotetradecen-1-ones employed in a particular instance can vary over a relatively wide range whereby specific desired organoleptic effects (having particular reference to the nature of the product) are achieved. Thus, correspondingly greater amounts would be necessary in those instances wherein the ultimate food composition to be flavored is relatively bland to the taste, whereas relatively minor quantities may suffice for purposes of enhancing the composition merely deficient in natural flavor or aroma. The primary requirement is that the amount selected be effective, i.e., sufficient to alter, modify, or enhance the organoleptic characteristics of the parent composition, whether foodstuff per se or flavoring composition.

The use of insufficient quantities of 2- and 3-cyclotetradecen-1-ones will, of course, substantially vitiate any possibility of obtaining the desired results while excess quantities prove needlessly costly and in extreme cases, may disrupt the flavor-aroma balance, thus proving self-defeating. Accordingly, the terminology "effective amount" and "sufficient amount" is to be accorded a significance in the context of the present invention consistent with the obtention of desired flavoring effects.

Thus, and with respect to ultimate food compositions, it has been found that quantities of 2- and 3- cyclotetradecen-1-ones ranging from a small but effective amount, e.g., 0.0001 parts per million up to about 50 parts per million by weight based on total composition are suitable. Concentrations in excess of the maximum quantity stated are not normally recommended, since they fail to provide commensurate enhancement or augmentation of organoleptic properties. In those instances wherein the 2- and 3-cyclotetradecen-1-ones are added to the foodstuff as an integral component of a flavoring composition, it is, of course, essential that the total quantity of flavoring composition employed be sufficient to yield an effective concentration (of 2- and 3-cyclotetradecen-1-ones) in the foodstuff product.

Food flavoring compositions prepared in accordance with the present invention preferably contain the 2- and 3-cyclotetradecen-1-ones in concentrations ranging from about 0.01% up to about 15% by weight based on the total weight of the said flavoring composition.

The compositions described herein can be prepared according to conventional techniques well known as typified by cake batters and fruit drinks and can be formulated by merely admixing the involved ingredients within the proportions stated in a suitable blender to obtain the desired consistency, homogeneity of dispersion, etc. Alternatively, flavoring compositions in the form of particulate solids can be conveniently prepared by mixing the 2- and 3-cyclotetradecen-1-ones with, for example, gum arabic, gum tragcanth, carrageenan and the like, and thereafter spray-drying the resultant mixture whereby to obtain the particulate solid product. Pre-prepared flavor mixes in powder form, e.g., a fruitflavored powder mix are obtained by mixing the dried solid components, e.g., starch, sugar and the like and 2- and/or 3-cyclotetradecen-1-ones in dry blender until the requisite degree of uniformity is achieved.

It is presently preferred to combine with 2- and 3-cyclotetradecen-1-ones, the following adjuvants:
p-Hydroxybenzyl acetone;
Geraniol;
Acetaldehyde;
Maltol;
Ethyl methyl phenyl glycidate;
Benzyl acetate;
Dimethyl sulfide;
Vanillin;
Methyl cinnamate;
Ethyl pelargonate;
Methyl anthranilate;
Isoamyl acetate;
Isobutyl acetate;
Alpha ionone;
β-Damascone;
β-Damascenone;
Ethyl butyrate;

Acetic acid;
n-Hexyl acetate;
n-Hexyl isobutyrate;
Trans-2-hexenal;
Linalyl isobutyrate;
n-Hexyl-2-methyl-n-butyrate;
Gamma-undecalactone;
Gamma-nonalactone;
Gamma decalactone;
Delta undecalactone;
Delta dodecalactone;
Delta nonyl lactone;
"Peach" lactone;
Naphthyl ethyl ether;
Diacetyl;
Apple Fusel Oil;
Sauge Sclaree;
Coriander Oil;
Ethyl acetate;
Anethole;
Isoamyl-n-butyrate;
Ethyl-2-methyl-cis-3-pentenoate;
Cis-3-hexenol-1;
2-Methyl-cis-3-pentenoic acid;
2-Methyl-2-pentenoic acid;
Elemecine (4-allyl-1,2,6-trimethoxy benzene);
Isoelemecine (4-propenyl-1,2,6-trimethoxy benzene); and
2-(4-hydroxy-4-methylpentyl) norbornadiene prepared according to U.S. Pat. No. 3,886,289.

The 2- and 3-cyclotetradecen-1-ones and one or more auxiliary perfume ingredients, including, for example, alcohols, aldehydes, nitriles, esters, cyclic esters, ketones other than the 2- and 3-cyclotetradecen-1-ones of our invention and natural essential oils, may be admixed so that the combined odors of the individual components produce a pleasant and desired fragrance particularly and preferably in musk and "animal-like" fragrances. Such perfume compositions usually contain (a) the main note or the "bouquet" or foundation stone of the composition; (b) modifiers which round off and accompany the main note; (c) fixatives which include odorous substances which lend a particular note to the perfume throughout all stages of evaporation and substances which retard evaporation; and (d) topnotes which are usually low boiling fresh smelling materials.

In perfume compositions, it is the individual components which contribute to its particular olfactory characteristics, but the over-all effect of the perfume composition will be the sum of the effects of each of the ingredients. Thus, the 2- and 3-cyclotetradecen-1-ones can be used to alter the aroma characteristics of a perfume composition, for example, by utilizing or moderating the olfactory reaction contributed by at least one other ingredient in the composition.

The amount of 2- and 3-cyclotetradecen-1-ones of our invention which will be effective in perfume compositions depends on many factors, including the other ingredients, their amounts and the effects which are desired. It has been found that perfume compositions containing as little as 0.01% of 2- and 3-cyclotetradecen-1-ones and even less (e.g., 0.005%) can be used to impart rich, animal-musk, and sweet notes as well as exaltonelike, scorched linen, waxy and rooty nuances to soaps, an ionic, cationic and nonionic detergents, fabric softener articles and compositions of matter, cosmetics or other products. The amount employed can range up to 10% of the fragrance components and will depend on considerations of cost, nature of the end product, the effect desired on the finished product and the particular fragrance sought.

The 2- and 3-cyclotetradecen-1-ones are useful, taken alone or in perfume compositions as olfactory components in anionic, cationic and nonionic detergents, soaps, fabric softener compositions, fabric softener articles for use in clothes dryers (e.g., "BOUNCE" ®, a registered trademark of the Procter & Gamble Company of Cincinnati, Ohio), space odorants and deodorants, perfumes, colognes, toilet water, bath preparations, such as bath oils, and bath solids; hair preparations, such as lacquers, brilliantines, creams, deodorants, hand lotions and sun screens; powders, such as talcs, dusting powders, face powders and the like. When used as an olefactory component in perfume compositions or perfumed articles, such as anionic, cationic and nonionic detergents and in fabric softener compositions and fabric softener articles (e.g., for use in clothing dryers) as little as 0.05% of the 2- and 3-cyclotetradecen-1-ones of our invention will suffice to impart an intense sweet musk fragrance with exaltone-like, scorched linen, waxy and rooty nuances. Generally, no more than 5% of the 2- and 3-cyclotetradecen-1-ones based on the ultimate end product is required in the perfume composition or in the perfumed article.

In addition, the perfume composition or fragrance composition of our invention can contain a vehicle or carrier for the 2- and 3-cyclotetradecen-1-ones. The vehicle can be a liquid such as a non-toxic alcohol, a non-toxic glycol, or the like. The carrier can also be an absorbent solid, such as a gum (e.g., gum arabic) or components for encapsulating the composition (such as gelatin) as by means of coacervation.

It will thus be apparent that the 2- and 3-cyclotetradecen-1-ones of our invention can be utilized to alter the sensory properties, particularly organoleptic properties, such as flavors and/or fragrances of a wide variety of consumable materials.

The following examples are illustrative and the invention is to be considered restricted thereto only as indicated in the appended claims. All parts and percentages given herein are by weight unless otherwise specified.

EXAMPLE I

PREPARATION OF 2- AND 3-CYCLOTETRADECEN-1-ONES

Reaction:

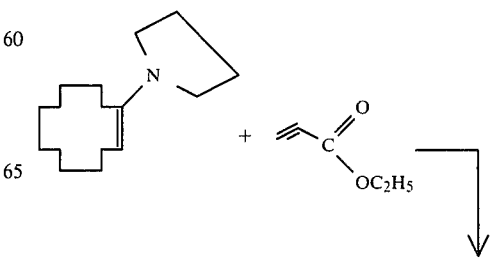

-continued

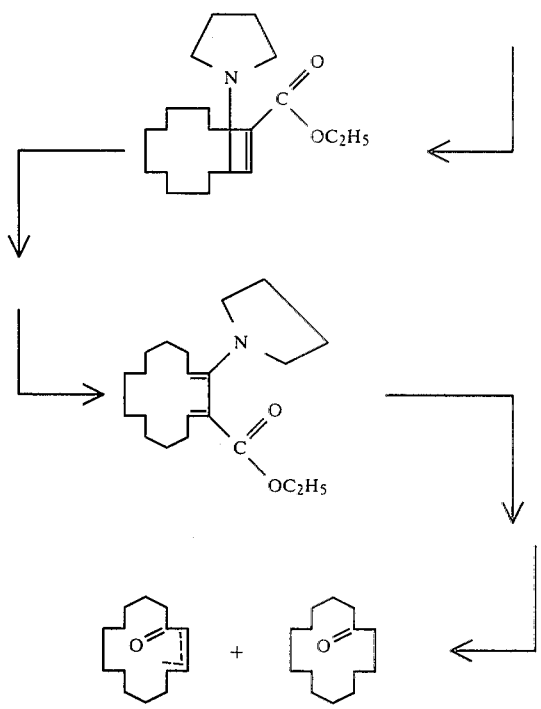

Into a 100 ml, three-necked reaction flask equipped with reflux condenser, magnetic stirrer, heating mantle, thermometer and addition funnel is added 17.4 gms of 1-(1-cyclododecen-1-yl)pyrrolidine (0.008 moles) and 25 ml of dry hexane. This mixture is brought to reflux and 6.8 gms of ethyl propiolate is added dropwise over a period of 15 minutes. After addition is completed, the reaction mass is cooled and hydrolyzed for twelve hours using 15% aqueous hydrochloric acid. At the end of this reaction period, the aqueous reaction mass is extracted with three 20 ml portions of diethyl ether and washed with two 20 ml portions of saturated sodium chloride. The resulting product is then dried over anhydrous magnesium sulfate and the solvent is removed yielding 17.0 gms of crude product. The recovered material is then distilled on a 8' micro Vigreux dolumn at reduced pressure yielding the following fractions:

| Fraction No. | Vapor Temp. (°C.) | Liquid Temp. (°C.) | Vac. mm. Hg. | Weight of Fraction Grams |
|---|---|---|---|---|
| 1 | 100/120 | 150/155 | 0.5/0.4 | 2.7 |
| 2 | 122 | 154 | 0.3 | 3.6 |
| 3 | 120 | 152 | 0.3 | 3.0 |
| 4 | 115 | 149 | 0.3 | 2.6 |
| 5 | 111 | 149 | 0.3 | 2.4 |
| 6 | 112 | 152 | 0.3 | 1.6 |
| 7 | 113 | 155 | 0.3 | 3.1 |
| 8 | 114 | 160 | 0.3 | 3.1 |
| 9 | 112 | 165 | 0.3 | 2.6 |
| 10 | 109 | 169 | 0.3 | 2.6 |
| 11 | 114 | 177 | 0.3 | 1.6 |
| 12 | 110 | 184 | 0.3 | 1.5 |
| 13 | 120 | 192 | 0.3 | 1.4 |
| 14 | 140 | 200 | 0.3 | 0.6 |
| 15 | 156 | 207 | 0.3 | 2.8 |
| 16 | 150 | 212 | 0.5 | |

Fractions 9, 10, 11, 12, 13 and 14 are then analyzed on a 4'×⅛" Carbowax 98 glass GLC column. Two peaks are obtained for each of fractions 9, 10, 11, 12, 13 and 14, the first peak of which has the structure:

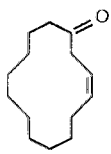

and the second peak of which has the structure:

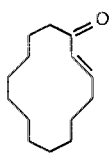

The compound having the structure:

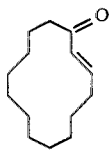

is all trans isomer. The compound having the structure:

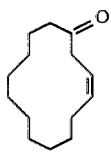

is a mixture of cis and trans isomers.

| Fraction No. | Peak for a Compound Having the Structure: 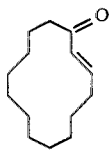 | Peak for a Compound Having the Structure: 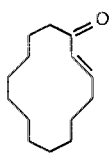 |
|---|---|---|
| 9 | 60.8% | 38.2% |
| 10 | 61.3% | 38.0% |
| 11 | 67.2% | 32.1% |
| 12 | 64.4% | 35.0% |
| 13 | 67.0% | 33.0% |
| 14 | 65.0% | 35.0% |

Fractions 2–7 from the 8' micro Vigreux column distillation are combined and redistilled on a 12" silver mirror automatic head distillation column yielding the following fractions:

| Fraction No. | Vapor Temp. (°C.) | Liquid Temp. (°C.) | Vac. mm. Hg. | Weight of Fraction Grams |
|---|---|---|---|---|
| 1 | 84/63 85 | 123/118 120 | .14/0.1 0.2 | 2.5 |
| 2 | 65 | 120 | 0.1 | 0.3 |
| 3 | 66 | 120 | 0.1 | 0.3 |

| Fraction No. | Vapor Temp. (°C.) | Liquid Temp. (°C.) | Vac. mm. Hg. | Weight of Fraction Grams |
|---|---|---|---|---|
| 4 | 62 | 118 | 0.15 | 0.3 |
| 5 | 71 | 120 | 0.15 | 0.3 |
| 6 | 65 | 118 | 0.1 | 0.3 |
| 7 | 66 | 118 | 0.1 | 0.3 |
| 8 | 69 | 123 | 0.1 | 0.4 |
| 9 | 82 | 127 | 0.1 | 2.7 |
| 10 | 83 | 141 | 0.1 | 2.8 |
| 11 | 75 | 200 | 0.1 | 1.2 |

The last fraction (fraction 11) is then analyzed on a 25'×0.25" 5% Carbowax 20 M GLC column (Conditions: isothermal at 250° C.; flow rate: helium gas at 100 ml per minute).

Figure 1:
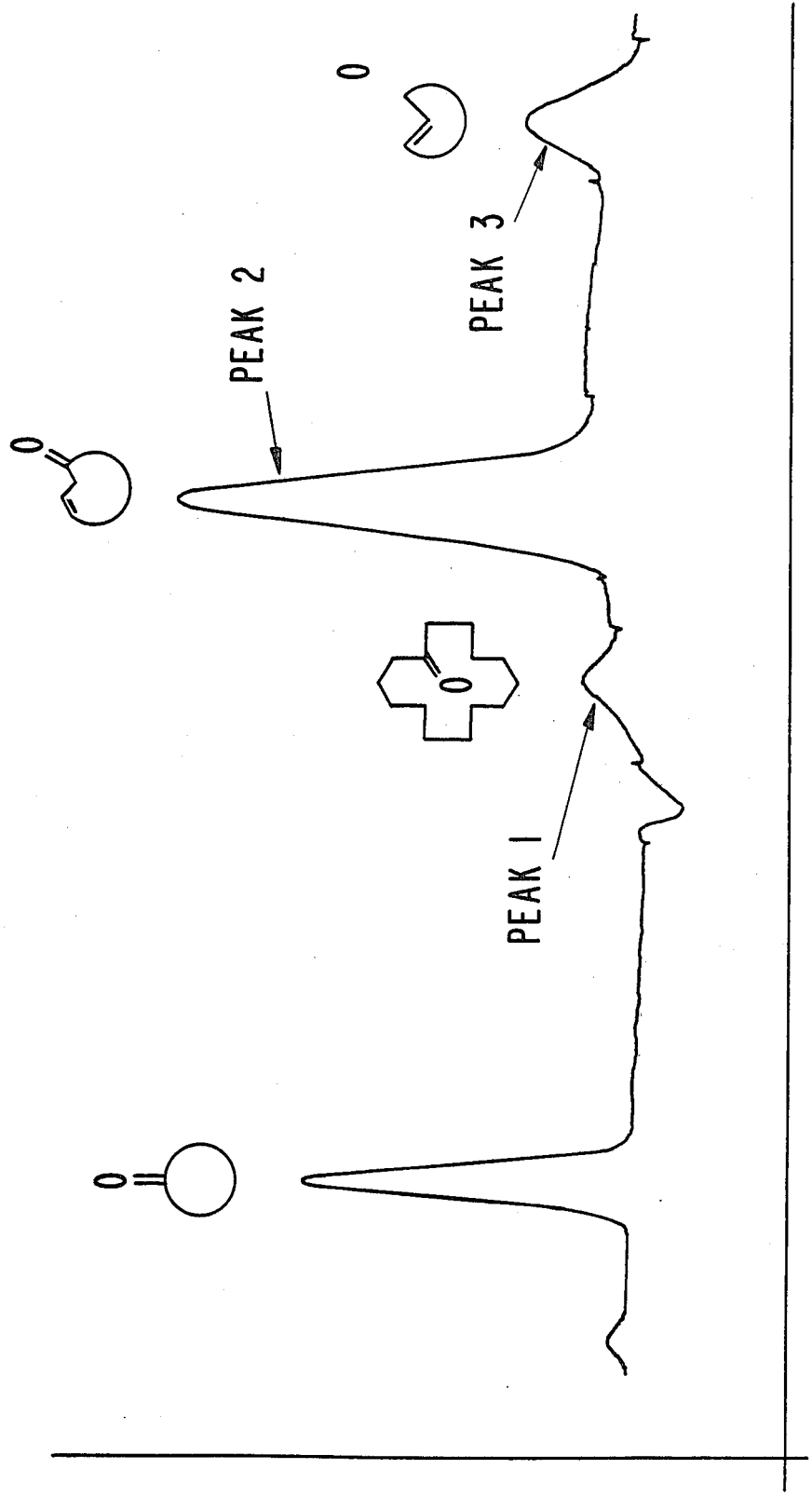
FIG. 1 is the GLC profile of the reaction product produced according to Example I wherein peak 1 represents cyclotetradecanone having the structure.

FIG. 1 represents the GLC profile for this product. Peak 1 has the structure:

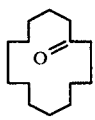

Peak 2 signifies the compound having the structure:

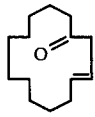

Peak 3 signifies the compound having the structure:

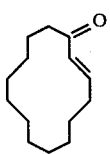

FIG. 2 is the NMR spectrum for peak 2.
FIG. 3 is the NMR spectrum for peak 3.
FIG. 4 is the infrared spectrum for peak 2.
FIG. 5 is the infrared spectrum for peak 3.

EXAMPLE II

The following basic pear flavor formulation is prepared:

| Ingredients | Parts by Weight |
|---|---|
| Vanillin | 2.0 |
| Hexyl Acetate | 8.0 |
| Hexyl Isobutyrate | 20.0 |
| Trans-2-hexenal (10% in propylene glycol) | 2.0 |
| n-Hexanal | 0.5 |
| Apple Fusel Oil | 10.0 |
| Linalyl Isobutyrate | 0.5 |
| Hexyl-2-methylbutyrate | 10.0 |
| Sauge Sclaree (10% in propylene glycol) | 0.5 |
| Coriander Oil | 0.5 |
| Food grade ethyl alcohol (aqueous, 95%) | 146.0 |
| Propylene glycol | 800.0 |

To a portion of the above basic pear flavor formulation, 0.02% by weight of a mixture containing 65% of the compound having the structure:

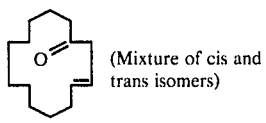 (Mixture of cis and trans isomers)

and 35% by weight of the compound having the structure:

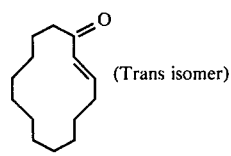 (Trans isomer)

produced according to Example I is added. To another portion of the basic pear flavor formulation, nothing is added. Both flavor formulations are compared at the rate of 50 ppm in water and evaluated by a bench panel of four experienced tasters. All the tasters of the bench panel state that the flavor containing the mixture of compounds having the structures:

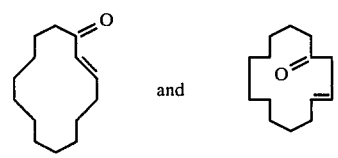

has a more natural riper pear character. This pear character is enhanced and longer lasting as a result of the addition of the compound having the structures:

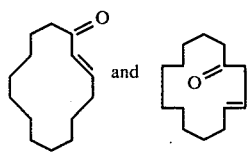

Therefore the flavor formulation containing the compounds having the structures:

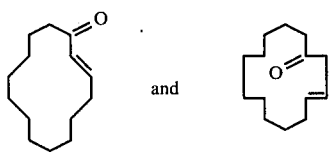

is preferred.

EXAMPLE III

A mixture of compounds containing 65% by weight of the compound having the structure:

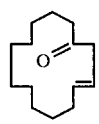

and 35% by weight of the compound having the structure:

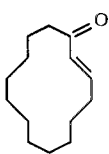

(prepared according to Example I) is added at the rate of 0.001 ppm to a cup of black coffee. At the rate of 0.001 ppm, the bitterness of the black coffee is significantly depressed compared with a cup of black coffee not containing said compounds having the structures:

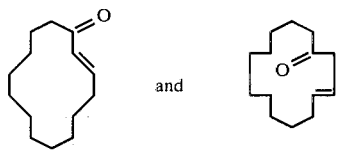

The said mixture of compounds added to the cup of black coffee at the rate of 0.001 ppm, is now made up into a solution containing 0.1% 2- and 3-cyclotetradecen-1-ones at the rate of 1% in 95% aqueous food grade ethanol. The 95% food grade ethanol solution of the 2- and 3-cyclotetradecen-1-ones is then added to water to cause the solution to be a concentration of 0.01% 2- and 3-cyclotetradecen-1-ones in the resulting solution. This solution is then sprayed onto roasted coffee grounds whereby the concentration of 2- and 3-cyclotetradecen-1-ones based on the dry weight of coffee grounds is 0.001 ppm. When the coffee grounds are extracted and used for producing coffee beverages whether with or without cream, the resulting coffee beverages' bitterness is significantly depressed compared to the said coffee beverages not containing the 2- and 3-cyclotetradecen-1-ones produced according to Example I.

EXAMPLE IV

Granular detergent compositions prepared according to United Kingdom Patent Specification No. 1,501,498 having the following formulae are prepared by spray-drying the following mixtures as indicated in the columns headed IV A, IV B, IV C and IV D.

| Ingredient | COMPOSITION IN % BY WEIGHT | | | |
|---|---|---|---|---|
| | Example IVA | Example IVB | Example IVC | Example IVD |
| Sodium salt of ethoxylated fatty alcohol sulfate having an average of about 2.25 moles of ethylene oxide per mole of fatty alcohol | 14.1 | 14.1 | 14.1 | 14.1 |
| Sodium tallow alkyl sulfate | 2.4 | 2.4 | 2.4 | 2.4 |
| Sodium silicate solids ratio: $SiO_2/Na_2O = 2.0$ | 0.0 | 2.0 | 6.0 | 0.0 |
| Sodium silicate solids ratio: $SiO_2/Na_2O = 3.2$ | 1.0 | 0.0 | 0.0 | 6.0 |
| Sodium tripolyphosphate | 24.0 | 24.0 | 24.0 | 24.0 |
| $Na_{12}(AlO_2 \cdot SiO_2)_{12} \cdot 27H_2O$ | 18.0 | 18.0 | 18.0 | 18.0 |
| Moisture | 10.0 | 10.1 | 9.9 | 10.2 |
| Sodium sulfate | 25.0 | 25.0 | 20.0 | 20.0 |
| Minor ingredients including sodium toluene sulfonate, trisodium sulfosuccinate, dyes, and brighteners | 4.0 | 2.4 | 3.6 | 2.3 |
| Mixture of 2- and 3-cyclotetradecen-1-ones prepared according to Example I | 1.5 | 0.0 | 0.0 | 0.0 |
| Compound having the structure: ![] prepared according to Example I | 0.0 | 2.0 | 0.0 | 0.0 |
| Compound having the structure: ![] prepared according to Example I | 0.0 | 0.0 | 2.0 | 0.0 |
| Mixture of compounds having the structures: ![] and ![] prepared according to Example I. | 0.0 | 0.0 | 0.0 | 5.0 |

Laundry solutions containing the above detergent compositions are used to launder fabrics. Each of the laundry compositions both prior to and on laundering gives rise to an intense musk aroma.

Each of the compositions of Example IVA, IVB, IVC and IVD has a sweet, musk aroma.

In addition, the composition of Example IVB has a scorched linen, waxy and rooty aroma. The composition of Example IVC has an exaltone-like undertone.

EXAMPLE V

PERFUMED LIQUID DETERGENT

Concentrated liquid detergents with animal-musky aromas are prepared containing 0.10%, 0.15% and 0.20% of a mixture of 2- and 3-cyclotetradecen-1-ones having the structures:

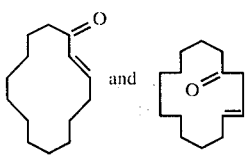

(35%) (trans isomer)  (65%) (mixture of cis and trans isomers)

prepared according to Example I. They are prepared by adding and homogeneously admixing the appropriate quantity of mixture of 2- and 3-cyclotetradecen-1-ones in liquid detergent. The liquid detergent is a builder-free liquid detergent consisting of (a) 50% of a non-ionic surfactant having an HLB of 8.0 and a critical micelle concentration of 0.007, weight % at 25° C; (b) an ionic surfactant which is triethanolamine citrate; and (c) 1 weight % of diethanolamine prepared according to United Kingdom Patent Specification No. 1,491,603.

The detergents all possess sweet musky fragrances, the intensity increasing with greater concentrations of mixture of 2- and 3-cyclotetradecen-1-ones.

EXAMPLE VI

A. POWDER FLAVOR

20 Grams of the flavor composition of Example II which flavor composition contains a mixture of 2- and 3-cyclotetradecen-1-ones is emulsified in a solution containing 300 grams gum acacia and 700 grams water. The emulsion is spray-dried with a Bowen Lab Model Drier utilizing 250 c.f.m. of air with an inlet temperature of 500° F., and outlet temperature of 200° F. and a wheel speed of 50,000 r.p.m.

B. PASTE BLEND

The following mixture is then prepared:

| Ingredients | Parts by Weight |
| --- | --- |
| Liquid Flavor Composition of Example II | 48.4 |
| Cab-O-Sil M-5 (Brand of Silica produced by the Cabot Corporation of 125 High Street, Boston, Mass., 02110); Physical Properties: Surface Area: 200m$^2$/gm Nominal Particle Size: 0.012 microns Density: 2/3 lbs./cu.ft. | 3.2 |

The Cab-O-Sil is dispersed in the liquid flavor composition with vigorous stirring, thereby resulting in a viscous liquid. 48.4 Parts by weight of the powder flavor composition prepared in Part A is then blended into the said viscous liquid, with stirring at 25° C. for a period of 30 minutes, resulting in a thixotropic sustained release flavor paste.

EXAMPLE VII

CHEWING GUM

100 Parts by weight of chicle are mixed with 4 parts by weight of the flavor prepared in accordance with Example VI. 300 Parts of sucrose and 100 parts of corn syrup are added. Mixing is effected in a ribbon blender with jacketed side walls of the type manufactured by the Baker Perkins Co.

The resultant chewing gum blend is then manufactured into strips 1 inch in width and 0.1 inches in thickness. The strips are cut into lengths of 3 inches each. On chewing, the chewing gum has a pleasant long-lasting pear flavor.

EXAMPLE VIII

TOOTHPASTE FORMULATION

The following separate groups of ingredients are prepared:

Group "A"

30.200—Glycerin
15.325—Distilled Water
0.100—Sodium Benzoate
0.125—Saccharin Sodium
0.400—Stannous Fluoride

Group "B"

12.500—Calcium Carbonate
37.200—Dicalcium Phosphate (Dihydrate)

Group "C"

2.000—Sodium n-Lauroyl Sarcosinate (foaming agent)

Group "D"

1.200—Flavor Material of Example VI
100.00 (Total)

PROCEDURE

1. To ingredients in Group "A" are stirred and heated in a steam jacketed kettle to 160° F.
2. Stirring is continued for an additional three to five minutes to form a homogeneous gel.
3. The powders of Group "B" are added to the gel, while mixing until a homogeneous paste is formed.
4. With stirring, the flavor of "D" is added and lastly the sodium n-lauroyl sarcosinate.
5. The resultant slurry is then blended for one hour. The completed paste is then transferred to a three roller mill and then homogenized, and finally tubed.

The resulting toothpaste when used in a normal toothbrushing procedure yields a pleasant pear flavor of constant strong intensity throughout said procedure (1–1.5 minutes).

EXAMPLE IX

CHEWABLE VITAMIN TABLETS

The flavor material produced according to the process of Example VI is added to a Chewable Vitamin Tablet Formulation at a rate of 5 gm/kg which Chewable Vitamin Tablet Formulation is prepared as follows:

| Ingredients | Gms/1000 Tablets |
| --- | --- |
| Vitamin C (ascorbic acid) as ascorbic acid-solution mixture 1:1 | 70.0 |
| Vitamin B$_1$ (thiamine mononitrate) as Rocoat ® thiamine mononitrate 33⁻% (Hoffman La Roche) | 4.0 |
| Vitamin B$_2$ (riboflavin) as Rocoat ® riboflavin 33⅓% | 5.0 |
| Vitamin B$_6$ (pyridoxine hydrochloride) as Rocoat ® pyridoxide hydrochloride 33⅓% | 4.0 |
| Niacinamide as Rocoat ® niacinamide 33⅓% | 33.0 |
| Calcium pantothenate | 11.5 |

-continued

| Ingredients | Gms/1000 Tablets |
|---|---|
| Vitamin B$_{12}$ (cyanocobalamin) as Merck 0.1% in gelatin | 3.5 |
| Vitamin E (dl-alpha tocophenyl acetate as dry Vitamin E acetate 33⅓% Roche | 6.6 |
| d-Biotin | 0.044 |
| Certified lake color | 5.0 |
| Flavor of Example VI | 5.0 |
| Sweetener sodium saccharin | 1.0 |
| Magnesium sterate lubricant | 10.0 |
| Mannitol q.s. to make | 500.0 |

Preliminary tablets are prepared by slugging, with flat-faced punches and grinding the slugs to 14 mesh. 13.5 g dry Vitamin A Acetate and 0.6 g Vitamin D are then added as beadlets. The entire blend is then compressed using concave punches at 0.5 g each.

Chewing of the resultant tablet yields a pleasant, long-lasting, consistently strong pear flavor for a period of 12 minutes.

EXAMPLE X

MUSK PERFUME FORMULATION

The following musk perfume formulation is prepared:

| Ingredients | Parts by Weight |
|---|---|
| Musk Ambrette | 200 |
| Musk Ketone | 200 |
| Beta Ionone | 50 |
| Vetiveryl Acetate | 50 |
| Sandalwood Oil | 100 |
| Benzyl Benzoate | 400 |
| Mixture of 2- and 3-cyclotetradecen-1-ones prepared according to Example I | 20 |

The mixture of 2- and 3-cyclotetradecen-1-ones of Example I imparts to this musk formulation, a natural "animal-musk" aroma and causes it to be more "natural-like".

EXAMPLE XI

PREPARATION OF A SOAP COMPOSITION

100 Grams of soap chips are mixed with 1 gram of the perfume composition of Example X until a substantially homogeneous composition is obtained. The perfumed soap composition manifests an excellent animal-musk aroma.

EXAMPLE XII

PREPARATION OF A SOAP COMPOSITION

100 Grams of soap chips are mixed with 1 gram of the 2- and 3-cyclotetradecen-1-ones prepared according to Example I until a substantially homogeneous composition is obtained. The perfumed soap composition manifests an excellent musk aroma.

EXAMPLE XIII

PREPARATION OF A COLOGNE AND HANDKERCHIEF PERFUME

The mixture of 2- and 3-cyclotetradecen-1-ones prepared according to Example I is incorporated into a cologne at concentrations of 1.5%, 2.0%, 2.5%, 3.0%, 3.5% and 4.0% in 85% aqueous ethanol; and into handkerchief perfumes at concentrations of 15%, 20%, 25% and 30% (in 95% aqueous ethanol). Distinct and definite animal-musk fragrances are produced and imparted to the cologne and to the handkerchief perfume at each of the levels indicated.

EXAMPLE XIV

PREPARATION OF A COSMETIC POWDER COMPOSITION

A cosmetic powder is prepared by mixing in a ball mill, 100 grams of talcum powder with 0.15 grams of the 2- and 3-cyclotetradecen-1-ones mixture prepared according to Example I. The resulting powder has an excellent musk aroma.

EXAMPLE XV

PREPARATION OF 2- AND 3-CYCLOTETRADECENONE MIXTURE

Ethyl propiolate (1.96 gm, 0.020 moles) in 5 ml sieve-dried heptane is placed in a 10 ml pressure-equalized Hershberg addition funnel in tandem atop a 14/20-jointed straight neck reflux condenser. In a 100 ml flame-dried, round bottom flask, crude 1-N-pyrrolidinocyclododecene (4.60 gm, 0.020 moles) in 15 ml heptane is brought to reflux under nitrogen. The oil bath is removed and the ethyl propiolate is added at a rate maintaining a vigorous reflux (approximately 3 minutes). The reaction mass is refluxed for an additional 15 minutes, and then the volatiles are removed under reduced pressure.

To the viscous residue, 45 ml of 18% aqueous hydrochloric acid is added. The reaction mass is then refluxed with vigorous stirring overnight. The resulting mixture is then cooled and extracted with three 50 ml volumes of diethyl ether. The combined ethereal layers are washed with saturated sodium bicarbonate (two 50 ml volumes) and brine. The resulting material is then dried over anhydrous magnesium sulfate. After solvent removal at reduced pressure, the resulting dark brown residue (4.20 gm) is Kugelrohr distilled (125° C. at 0.1 mm Hg) and yields a light yellow oil (3.54 gm). Chromatography on Silica gel (50 gm) with 3% ethylacetate-pentane affords the cyclododecanone (0.298 gm, 16%) and 2.85 gm cyclotetradecenones as a roughly 1:1 $\alpha,\beta:\beta,\gamma$ unsaturated ketone mixture (0.0136 moles, 68% based on cyclodedecanone precursor).

The individual unsaturated ketone isomers isolated by preparative thin layer chromatography are identified as follows:

| E-2-Cyclotetradecenone | | |
|---|---|---|
| IR: | 1691 | sharp, strong |
| | 1620 | broadened, medium |
| | 980 | broad doublet, medium-strong |
| NMR: | 1.28 | singlet (19.1 H) |
| | 2.32 multiplet (2.3 H) | |
| | 2.43 | doublet, J = 7.0 Hz (1.8 H) |
| | 6.18 | doublet, J = 15.5 Hz (1.0 H) |
| | 6.90 | doublet of triplets, J = 15.5 and 7.0 Hz (1.0 H) |
| UV: | $\lambda_{max}^{EtOH}$ = 224 m$\mu$, $\epsilon$ = 6900 (reported[88] $\lambda_{max}^{EtOH}$ = 226 m$\mu$, $\epsilon$ = 3875) | |
| MS(20 eV): | 208(100%), 98(74%), 96(51%) | |
| E- and Z-3-Cyclotetradecenone | | |
| IR: | 1718 | sharp, strong |
| | 1650 | broadened, weak |
| NMR: | 1.28 | singlet (16.6 H) |
| | 2.18 | multiplet (2.4 H) |
| | 2.42 | triplet J = 7.5 Hz (2.2 H) |
| | 2.88 and 3.17 | two broadened doublets in a 3:1 ratio. |

-continued

| | J | 6.0 Hz for both (2.0 H total) |
|---|---|---|
| | 5.48 | multiplet (2.0 H) |
| MS(20 eV): | 208(100%), 182(62%), 96(69%), 81(74%) | |

EXAMPLE XVI

Utilizing the procedure of Example I of column 15 of U.S. Pat. No. 3,632,396, a nonwoven cloth substrate useful as a dryer-added fabric-softening article of manufacture is prepared wherein the substrate, the substrate coating and the outer coating and the perfuming material are as follows:
1. a water "dissolvable" paper (Dissolvo" Paper);
2. Adogen 448 (m.p. about 140° F.) as the substrate coating; and
3. an outer coating having the following formulation (m.p. about 150° F.):
   57 percent $C_{20-22}$ HAPS
   22 percent isopropyl alcohol
   20 percent antistatic agent
   1 percent of the mixture of 2- and 3-cyclotetradecen-1-ones having the structures:

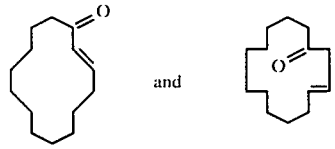

and cyclotetradecanone having the structure:

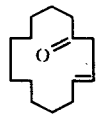

prepared according to Example I.

Fabric-softening compositions prepared as set forth above having an aroma characteristic which can be described as sweet and musky with exaltone-like nuances essentially consist of a substrate having a weight of about 3 grams per 100 square inches, a substrate coating of about 1.85 grams per 100 square inches of substrate and an outer coating of about 1.4 grams per 100 square inches of substrate thereby providing a total aromatized substrate and an outer coating weight ratio of about 1:1 by weight of the substrate. A sweet, musky, exaltone-like aroma is imparted in a pleasant manner to the head space in the dryer on operation thereof using the said dryer added fabric softening nonwoven fabric.

EXAMPLE XVII

Utilizing the procedure of Example I of column 15 of U.S. Pat. No. 3,632,396, a nonwoven cloth substrate useful as a dryer-added fabric-softening article of manufacture is prepared wherein the substrate, the substrate coating and the outer coating and the perfuming material are as follows:
1. a water "dissolvable" paper ("Dissolvo"Paper);
2. Adogen 448 (m.p. about 140° F.) as the substrate coating; and
3. an outer coating having the following formulation (m.p. about 150° F.):
   57 percent $C_{20-22}$ HAPS
   22 percent isopropyl alcohol
   20 percent antistatic agent
   1.5 percent of the mixture of 2- and 3-cyclotetradecen-1-ones and cyclododecanone prepared according to Example XV.

A fabric-softening composition prepared as set forth above having an aroma characteristic which can be described as sweet, musky and exaltone-like essentially consists of a substrate having a weight of about 3 grams per 100 square inches, a substrate coating of about 1.85 grams per 100 square inches of substrate and an outer coating of about 1.4 grams per 100 square inches of substrate, thereby providing a total aromatized substrate and an outer coating weight ratio of about 1:1 by weight of the substrate. The resulting aroma is described as sweet, musky and exaltone-like and is imparted in a pleasant manner to the head space in the dryer on operation thereof using the said dryer added fabric softening nonwoven fabric.

EXAMPLE XVIII

PREPARATION OF A SOAP COMPOSITION

100 Grams of soap chips are prepared according to Example V of U.S. Pat. No. 4,058,490, issued on Nov. 15, 1977 as follows:

"The sodium salt of an equal mixture of $C_{10}/C_{14}$ alkane sulfonates (95% active, 40 lbs. is dissolved in a mixture of 80 lbs. of anhydrous isopropanol and 125 lbs. of deionized water at 150° F. In this mixture is dissolved 10 lbs. of partially hydrogenated coconut oil fatty acids and 15 lbs. of sodium mono-$C_{14}$-alkyl maleate, and the pH of this solution is adjusted to 6.0 by the addition of a small amount of a 50% aqueous solution of NaOH. The isopropanol is distilled off and the remaining aqueous solution is dried. The resulting solid actives are then blended in a chip mixer with 10 lbs. water, 0.2 lb. titanium hydroxide"

The resulting blend is then mixed with 1 gm of the compound having the structure:

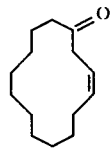

(a cis trans isomer mixture)

until a substantially homogeneous composition is obtained. The perfumed soap composition manifests an excellent sweet, musk, exaltone-like aroma.

EXAMPLE XIX

PREPARATION OF A SOAP COMPOSITION

100 Grams of soap chips are prepared according to Example V of U.S. Pat. No. 4,058,490, issued on Nov. 15, 1977 as follows:

"The sodium salt of an equal mixture of $C_{10}/C_{14}$ alkane sulfonates (95% active), 40 lbs. is dissolved in a mixture of 80 lbs. of anhydrous isopropanol and 125 lbs. of deionized water at 150° F. In this mixture is dissolved 10 lbs. of partially hydrogenated coconut oil fatty acids and 15 lbs. of sodium mono-$C_{14}$-alkyl maleate, and the pH of this solution is adjusted to 6.0 by the addition of a small amount of a 50% aqueous solution of NaOH. The isopropanol is distilled off and the remaining aqueous solution is dried. The resulting solid actives are then blended in a chip mixer with 10 lbs. water, 0.2 lb. titanium hydroxide"

The resulting blend is then mixed with 1 gm of the compound having the structure:

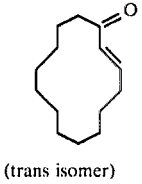

(trans isomer)

until a substantially homogeneous composition is obtained. The perfumed soap composition manifests an excellent musk aroma with a scorched linen, waxy and rooty topnote profile.

What is claimed is:

1. A process for augmenting or enhancing the aroma of a fabric softener article which fabric softener article comprising a paper or cloth substrate, a waxy, cationic or nonionic substrate coating material, and an outer coating consisting essentially of a fabric softener composition, said process comprising the step of intimately admixing with said outer coating composition an aroma augmenting or enhancing quantity of a product which comprises a mixture of 2- and 3-cyclotetradecen-1-ones having the structures:

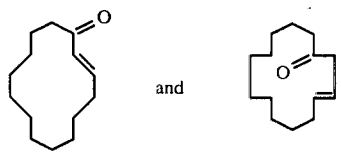

and cyclotetradecanone having the structure:

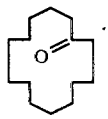

produced according to the process defined according to the reaction sequence:

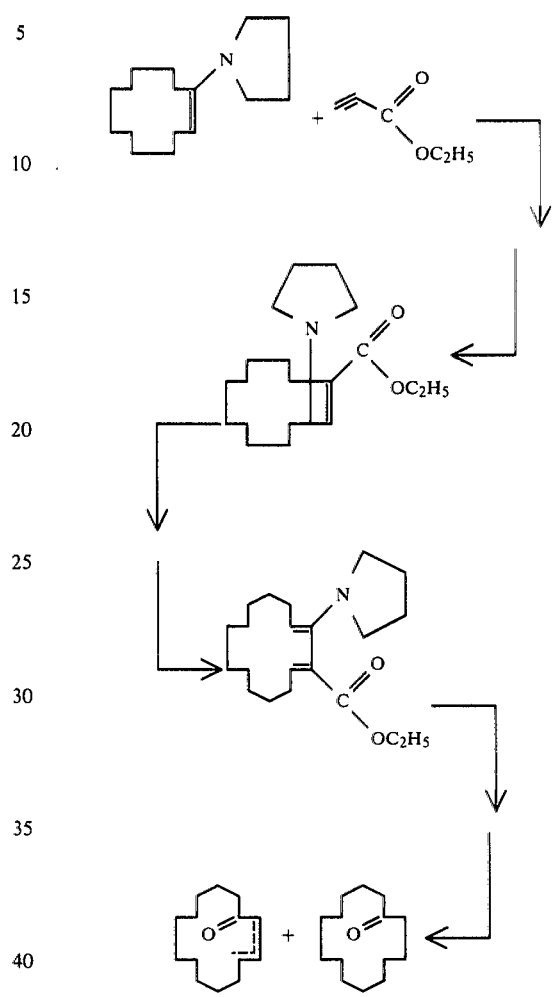

wherein one of the dashed lines represents a carbon-carbon single bond and the other of the dashed lines represents a carbon-carbon double bond, coating the substrate with the substrate coating and then coating the substrate coating with the outer coating comprising said product by process which contains the 2- and 3-cyclotetradecen-1-ones and the cyclotetradecanone.

* * * * *